United States Patent [19]

Drent

[11] Patent Number: 4,461,910

[45] Date of Patent: Jul. 24, 1984

[54] PROCESS FOR THE CO-PRODUCTION OF DICARBOXYLATES AND ACIDS

[75] Inventor: Eit Drent, Amsterdam, Netherlands

[73] Assignee: Shell Oil Company, Houston, Tex.

[21] Appl. No.: 355,957

[22] Filed: Mar. 8, 1982

[30] Foreign Application Priority Data

May 15, 1981 [GB] United Kingdom ............... 8114907

[51] Int. Cl.$^3$ ............... C07C 51/083; C07C 67/00; C07C 67/12; C07C 69/003; C07C 69/007
[52] U.S. Cl. ................... 560/263; 260/408; 260/409; 260/410.6; 260/413; 560/8; 560/73; 560/102; 560/106; 560/112; 560/186; 560/187; 560/229; 560/232; 560/261; 562/405; 562/473; 562/492; 562/493; 562/587; 562/588; 562/602; 562/606; 562/607
[58] Field of Search ............... 560/263, 106, 112, 232, 560/8, 73, 102, 186–187, 229; 562/405, 493, 492, 598, 606, 607, 473, 602, 587, 588; 260/409, 410.6, 413, 408

[56] References Cited

U.S. PATENT DOCUMENTS

| | | | |
|---|---|---|---|
| 3,579,566 | 5/1971 | Fenton | 560/263 |
| 4,221,918 | 9/1980 | Suzuki | 560/263 |

FOREIGN PATENT DOCUMENTS 1538782  1/1979  United Kingdom ............... 560/232

*Primary Examiner*—Vivian Garner
*Attorney, Agent, or Firm*—Ronald R. Reper

[57] ABSTRACT

A process for the co-production of an alkylidene dicarboxylate and a carboxylic acid, which comprises hydrogenating a carboxylic acid anhydride in the presence of carbon monoxide and a homogeneous iridium- and/or rhodium-containing catalyst, together with an organo phosphorus (III), arsenic (III), or antimony (III) compound and either molecular oxygen or a phosphorus (V), arsenic (V) or antimony (V) compound containing a X=O moiety, where X is a phosphorus, arsenic or antimony atom.

9 Claims, No Drawings

PROCESS FOR THE CO-PRODUCTION OF DICARBOXYLATES AND ACIDS

BACKGROUND OF THE INVENTION

This invention relates to a process for the co-production of dicarboxylates and acids.

U.S. Pat. No. 3,579,566 discloses that the hydrogenation of a carboxylic acid anhydride to give an alkylidene dicarboxylate plus an acid may be carried out using a catalyst comprising a complex of a Group VIII noble metal with a trihydrocarbyl phosphine, stilbine or arsine. However, the reaction products obtained by this process are complex mixtures, and the yield of the desired dicarboxylate is very low. In particular, the carboxylic acid which, according to the stoichiometry of the reaction should be formed in a quantity equimolar with the dicarboxylate, is formed in large excess. Thus, in Example 1 of the specification, the molar ratio of acetic acid to ethylidene diacetate is 6.7:1. Further, the temperatures and pressures required for the reaction are very high.

It has now been found that by the use of a specific catalyst-promoter system in the reaction of hydrogen with a carboxylic acid anhydride, the process can be carried out giving good yield and high selectivity to the desired products.

SUMMARY OF THE INVENTION

The invention therefore provides a process for the co-production of an alkylidene dicarboxylate and a carboxylic acid, which process comprises hydrogenating a carboxylic acid anhydride in the presence of carbon monoxide and a homogeneous iridium- and/or rhodium-containing catalyst, together with an organo phosphorus (III), arsenic (III) or antimony (III) compound and either molecular oxygen or a phosphorus (V), arsenic (V) or animony (V) compound containing an X=O moiety where X is a phosphorus, arsenic or antimony atom.

DESCRIPTION OF PREFERRED EMBODIMENTS

A wide range of carboxylic acid anhydrides can be used as starting material in the process according to the invention. In general terms, the reaction proceeds according to the equation:

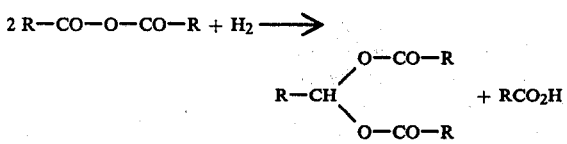

wherein R is an organo group containing up to 20 carbon atoms. Preferably a symmetrical anhydride is used as feedstock, so that only a single dicarboxylate and a single carboxylic acid are produced. However, the reduction can if desired be carried out using a mixed anhydride (i.e., the R's are different) in which case a mixture of products is obtained. In certain circumstances, the groups R in the product may differ from the groups R in the anhydride. For example, if an R in the anhydride contains an olefinic double bond, this will be hydrogenated under the reaction conditions and products containing the corresponding saturated R group will be obtained.

Preferably, each R in the anhydride independently represents an alkyl, alkenyl, alkynyl or aryl group, which may if desired be substituted by one or more substituents, for example halogen atoms, phenyl groups and alkoxy groups, but are preferably unsubstituted, and preferably have up to 20 carbon atoms. More preferably each R represents an unsubstituted alkyl group having up to 6 carbon atoms. Acetic anhydride is an especially preferred starting material, in which case the reaction products are ethylidene diacetate and acetic acid.

Suitable hetero organo compounds are chosen containing an element selected from phosphorus, arsenic, and animony; each said element being in the trivalent (III) state.

Suitable organo phosphorus (III), arsenic (III) and antimony (III) compounds include those of the general formula

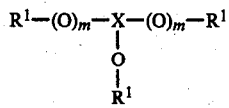

in which X is a phosphorus, antimony or arsenic atom, each m independently represents 0 or 1, and each $R^1$ independently represents alkyl, cycloalkyl or aryl group, having up to 20 carbon atoms—which group may optionally be substituted or unsubstituted, or one $R^1$ has this meaning and the other two $R^1$'s together represent an alkylene group. Optional substituents may be any moieties inert under the reaction conditions, for example halogen atoms, alkoxy groups, phenyl groups and $-XR^1_2$ groups.

Preferably each m represents 0.

Preferred compounds are those of the formula

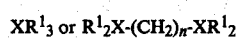

where n is 1, 2 or 3 and each $R^1$ independently represents a hydrocarbyl group having up to 20 carbon atoms.

Preferably $R^1$ may be any alkyl group having up to 20 carbon atoms; any cycloalkyl group having up to 7 carbon atoms; any aryl group and more preferably is a phenyl group; and any alkylene group having up to 20 carbon atoms.

Especially preferred phosphorus, arsenic or antimony (III) compounds are those in which each m is 0 and each $R^1$ independently represents an alkyl or a phenyl group. For economic reasons, it is generally preferred that each $R^1$ represents the same group. Typical specific compounds include trimethylphosphine, triethylphosphine, tributylphosphine and triphenylphosphine, and their arsenic or antimony analogues. In general, the use of a phosphorus (III) compound rather than an antimony (III) or arsenic (III) compound is preferred.

The amount of phosphorus, antimony or arsenic (III) compound present is not crucial. The ratio of said compound to catalyst may for example be in the range of from 1:1 to 20:1, especially 2:1 to 10:1, calculated as moles of said compound per gram atom of rhodium plus iridium present.

The pentavalent, compound, i.e. phosphorus (V), arsenic (V) or antimony (V), compound containing an X=O moiety may for example be an oxide of the general formula $O=XR^1_3$, where each $R^1$ independently has one of the meanings given above. Typical compounds of this type include the oxides of the specific phosphorus, arsenic or antimony (III) compounds listed above. Alternatively, the compound may be an oxyacid or derivative thereof of the general formula

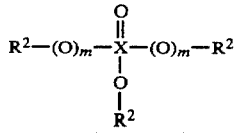

in which each m independently represents 0 or 1 and each $R^2$ independently has one of the meanings previously given for $R^1$ or represents a hydrogen atom. Typical compounds of this type include phosphoric acid and its mono-, di- or tri-alkyl esters, especially its lower alkyl esters, wherein these alkyl groups contain from 1 to 4 carbon atoms, for example tri-n-butyl phosphate. In general, the use of a phosphorus (V) compound rather than an antimony (V) or arsenic (V) compound is preferred.

The process according to the invention may be carried out in the presence of molecular oxygen rather than an added X=O containing compound. It is possible, but not confirmed, that the effect of the oxygen is to oxidize part of the trivalent compound present, thus generating the corresponding oxide in situ. It is of course normal practice when conducting reductions by homogeneous catalysts, to exclude oxygen carefully from the reaction system to avoid oxidation of the catalyst from its active form to in inactive form, and it is most surprising that in the process according to the invention the presence of oxygen has a beneficial effect.

The phosphorus, arsenic or antimony (V) compound or molecular oxygen is present in the reaction mixture in catalytic quantities, but the precise amount is not crucial. Suitably the molar ratio of said compound or molecular oxygen to phophorus, arsenic or antimony (III) compound is in the range of from 0.05:1 to 5:1, and especially from 1.1 to 2.5:1.

The iridium- and/or rhodium-containing catalyst comprises these metals in any of the forms generally used in homogeneous catalytic reactions. The metal may for example be added to the reaction mixture in the form of a salt with a mineral acid, for example a halide, nitrate or sulphate, or with an organic acid, for example a carboxylate having up to 20 carbon atoms, especially an alkanoate, such as an acetate. Alternatively, the metal may be in zero valent form complexed by ligands such as the phosphorus (III) ligands described above, carbon monoxide, or acetylacetonates. The precise form of the active species involved in the catalysis is of course not known: it may be the compound added, or it may be a species generated in situ. The catalyst must however be homogeneous with the reaction medium, and the presence of carbon monoxide is necessary in order to stabilize the catalyst in solution. The carbon monoxide is suitably provided in admixture with the hydrogen gas supplied to the system. The relative amounts of hydrogen and carbon monoxide supplied to the system may vary over a very wide range. For example, a molar ratio $H_2:CO$ in the range 1:99 to 99:1 is suitable, with a molar ratio range of 25:75 to 95:5 being preferred.

The quantity of catalyst present in the system is generally determined by economic considerations. Quantities of catalyst of between 0.001 to 10, especially 0.05 to 5, mole % based on the number of moles of anhydride, are generally suitable. Preferably, a rhodium-containing catalyst is used.

As stated above, the hydrogen gas stream supplied to the system may contain carbon monoxide. It may also if desired contain inert gases, such as nitrogen. The reaction is suitably carried out under a pressure within the range of from 10 to 150 bars, especially from about 20 to 100 bars. High pressures, for example up to 1000 bars, can of course be used, but are generally undesirable for economic reasons.

The reaction temperature is suitably in the range of from 100° to 200° C., especially from about 130° to 170° C.

The reaction is suitably carried out under substantially anhydrous conditions to prevent hydrolysis of the starting material and the product. However, the presence of minor amounts of water such as those normally found in the commercial forms of the components of the reaction mixture presents no problem.

The process according to the invention is often conveniently carried out using excess carboxylic acid anhydride as solvent. However, if desired, any suitable additional solvent may be used. Suitable inert solvents include hydrocarbons, for example xylene or hexane, ethers, for example tetrahydrofuran, amides, for example dimethyl-formamide, nitriles, for example acetonitrile, and sulphur-containing compounds, for example sulpholane.

In a preferred embodiment of the process according to the invention the carboxylic acid anhydride used as starting material has been prepared in a separate reaction step by the carbonylation of an ester in the presence of a suitable catalyst. Suitable methods for carrying out this carbonylation are described for example in British Patent Specification Nos. 1523346 and 1468940 incorporated herein by reference.

The alkylidene dicarboxylate produced by the process according to the invention may be converted into a number of other valuable products by known methods, for example into olefinic esters, or into aldehydes. For example, ethylidene diacetate, which is the preferred compound produced by the process according to the invention, can be converted into either vinyl acetate or acetaldehyde by well known methods.

Thus, for example in an integrated reaction scheme, methanol, carbon monoxide and hydrogen can be converted into vinyl acetate:

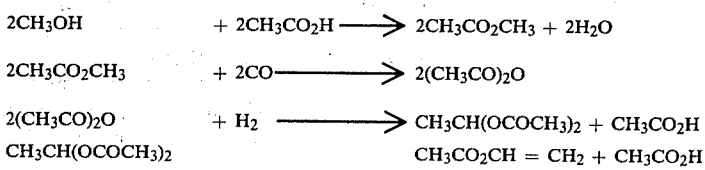

-continued $$2CH_3OH + 2CO + H_2 \longrightarrow CH_3CO_2CH=CH_2 + 2H_2O.$$

Alternatively, the ethylidene diacetate can be converted into acetaldehyde:

$$CH_3CH(OCOCH_3)_2 \longrightarrow CH_3CHO + (CH_3CO)_2O$$

and the overall reaction becomes:

$$CH_3OH + CO + H_2 \longrightarrow CH_3CHO + H_2O.$$

The following Examples illustrate the invention.

EXAMPLE 1

A Hastelloy C (Trade Mark) 300 Ml magnet-driven autoclave was charged with 50 mls acetic anhydride, 1 mmol rhodium trichloride, 2.3 mmol triphenylphosphine and 0.35 mmol triphenylphosphine oxide, flushed with carbon monoxide, and then pressurized to 40 bars with a 1:1 molar mixture of carbon monoxide and hydrogen. The autoclave was then maintained at 15° C. for 15 hours. The contents were cooled and analysed using gas-liquid chromatography. 50%m of the acetic anhydride had been converted to acetic acid and ethylidene diacetate in a molar ratio of 1.4:1. Only traces of other products were obtained.

EXAMPLE 2

Example 1 was repeated, except that the triphenylphosphine oxide was replaced by 0.4 mmol of dimethyl methyl phosphonate, $CH_3.PO.(OCH_3)_2$. The conversion of acetic anhydride was 30%m, and the ratio of acetic acid to ethylidene diacetate was 1:1.

EXAMPLE 3

Example 1 was repeated except that the triphenyl phosphine oxide was replaced by 0.4 mmol of tributyl phosphate. The conversion of acetic anhydride was 33%m, and the ratio of acetic acid to ethylidene diacetate was 1.1:1.

EXAMPLE 4

A Hastelloy C (Trade Mark) 300 ml magnet-driven autoclave was charged with 50 mls acetic anhydride, 1 mmol rhodium trichloride and 2.5 mmol triphenylphosphine. The autoclave was then pressurized with 1 bar air and 40 bars of a 1:1 molar CO:H$_2$ mixture. The autoclave was maintained at 150° C. for 15 hours. Analysis of the contents showed a conversion of acetic anhydride of 40%m, and a ratio of acetic acid to ethylidene diacetate of 1.3:1.

EXAMPLES 5 to 7 (comparison)

The method of Example 1 was repeated except that a number of catalyst systems outside the scope of this invention were used. The results are given in the following Table. In all cases, it can be seen that the selectivity to the desired ethylidene diacetate is very poor.

I claim as my invention:

1. A process for the co-production of an alkylidene dicarboxylate and a carboxylic acid, which comprises hydrogenating a carboxylic acid anhydride of the general formula R—CO—O—CO—R, in which each R independently represents an organo group having up to 20 carbon atoms selected from an alkyl, alkenyl, alkynyl, and aryl, at a temperature from 100° to 200° C. and pressure from 10 to 150 bars in the presence of carbon monoxide and a homogeneous iridium- and/or rhodium-containing catalyst, together with an organo phosphorus (III), arsenic (III) or antimony (III) compound and component selected from the group consisting of molecular oxygen and compounds selected from the group consisting of compounds containing an X=O moiety, wherein X is selected from the group consisting of phosphorus (V), arsenic (V), and antimony (V), said X=O moiety compounds having the general formula

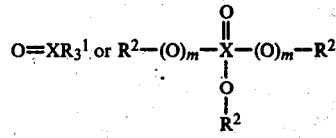

in which X represents a phosphorus, arsenic or antimony atom, each m independently is 0 or 1, each R$^1$ independently represents an organo group having up to 20 carbon atoms selected from the group consisting of alkyl, cycloalkyl and aryl, or one R$^1$ has this meaning and the other two R$^1$'s, together represent one alkylene group, said organo group may optionally bear at least one substituent selected from the group consisting of halogen atoms, alkoxy groups and phenyl groups, and each R$^2$ independently represents R$^1$ or a hydrogen atom.

2. A process as in claim 1, in which the organo phosphorus (III), arsenic (III) or antimony (III) compound has the general formula

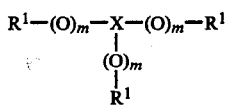

TABLE

| Example No. | Catalyst Components | (mmol) | Conversion of Anhydride (% m) | Ratio Acetic Acid To Ethylidene Diacetate | Comments |
|---|---|---|---|---|---|
| 5 | RhCl$_3$ | 1.0 | 10 | 2.6:1 | Phosphorus (III) only |
|   | P(phenyl)$_3$ | 2.5 | | | |
| 6 | RhCl$_3$ | 1.0 | 15 | 5.6:1 | No phosphorus (III) |
|   | O=P(phenyl)$_3$ | 2.5 | | | |
| 7 | Pd(O.CO.CH$_3$)$_2$ | 1.0 | 2 | 7.7:1 | Palladium catalyst |
|   | P(phenyl)$_3$ | 2.3 | | | |
|   | O=P(phenyl)$_3$ | 0.35 | | | | in which X is a phosphorus, arsenic, or antimony atom, each m independently represents 0 or 1 and each $R^1$ independently represents an organo group having up to 20 carbon atoms selected from the group consisting of alkyl, cycloalkyl, and aryl, or one $R^1$ has this meaning and the other two $R^1$'s together represent an alkylene group, said organo group may optionally bear at least one substituent selected from the group consisting of halogen atoms, alkoxy groups, and phenyl groups.

3. A process as in claim 1, in which the organo phosphorus (III), arsenic (III), or antimony (III) compound has the formula $$XR^1_3 \text{ or } R^1_2X\text{-}(CH_2)_n\text{-}XR^1_2$$

in which X is a phosphorus, arsenic, or antimony atom, n is 1, 2, or 3 and each $R^1$ independently represents a hydrocarbyl group having up to 20 carbon atoms.

4. A process as in claim 1, in which an organo phosphorus (III) compound is used.

5. A process as in claim 1, in which each $R^1$ independently represents a hydrocarbyl group, and each $R^2$ independently represents a hydrocarbyl group or hydrogen atom.

6. A process as in claim 1, in which a phosphorus (V) compound containing a P=O moiety is used.

7. A process as in claim 1, in which the molar ratio of phosphorus (V), arsenic (V) or antimony (V) compound or molecular oxygen to phosphorus (III), arsenic (III) or antimony (III) compound is in the range of from 0.05:1 to 5:1.

8. A process as in claim 1, in which a rhodium-containing catalyst is used.

9. A process for the co-production of an alkylidene dicarboxylate and a carboxylic acid, which comprises hydrogenating a carboxylic acid anhydride of the general formula R—CO—O—CO—R, in which both R's are the same and represent an unsubstituted alkyl group having up to 6 carbon atoms, at a temperature from 100° to 200° C. and pressure from 10 to 150 bars in the presence of carbon monoxide and a homogeneous iridium- and/or rhodium-containing catalyst, together with an organo phosphorus (III), arsenic (III) or antimony (III) compound and component selected from the group consisting of molecular oxygen and compounds selected from the group consisting of compounds containing an X=O moiety, wherein X is selected from the group consisting of phosphorus (V), arsenic (V), and antimony (V), said X=O moiety compounds having the general formula

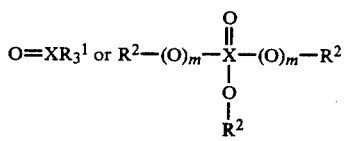

in which X represents a phosphorus, arsenic or antimony atom, each m independently is 0 or 1, independently represents an organo group having up to 20 carbon atoms selected from the group consisting of alkyl, cycloalkyl and aryl, or one $R^1$ has this meaning and the other two $R^1$'s together represent one alkylene group, said organo group may optionally bear at least one substituent selected from the group consisting of halogen atoms, alkoxy groups and phenyl groups, and each $R^2$ independently represents $R^1$ or a hydrogen atom.

* * * * *